US008470262B2

(12) United States Patent
Karaki et al.

(10) Patent No.: US 8,470,262 B2
(45) Date of Patent: Jun. 25, 2013

(54) MICROFLUIDIC DEVICE

(75) Inventors: Hideyuki Karaki, Kanagawa (JP); Yoshihiro Sawayashiki, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 179 days.

(21) Appl. No.: 13/024,079

(22) Filed: Feb. 9, 2011

(65) Prior Publication Data

US 2011/0194978 A1 Aug. 11, 2011

(30) Foreign Application Priority Data

Feb. 10, 2010 (JP) ................................ P2010-028265

(51) Int. Cl.
*G01N 15/06* (2006.01)
*G01N 33/00* (2006.01)
*G01N 33/48* (2006.01)

(52) U.S. Cl.
USPC ............ 422/503; 422/68.1; 422/502; 436/43; 436/63

(58) Field of Classification Search
USPC ........................................ 422/68.1, 502, 503
See application file for complete search history.

(56) References Cited

U.S. PATENT DOCUMENTS 6,755,211 B1 * 6/2004 O'Connor et al. ............ 137/554

FOREIGN PATENT DOCUMENTS

JP 2006-337221 A 12/2006

* cited by examiner

*Primary Examiner* — Brian J Sines
(74) *Attorney, Agent, or Firm* — Birch, Stewart, Kolasch & Birch, LLP

(57) ABSTRACT

It is a microfluidic device including a flowchannel in which liquid flows. The flowchannel includes a main channel and a pair of branch channels provided across the main channel from each other to be each connected to the main channel. The main channel includes a first zone, a second zone, and a coupling zone that connects the first zone and the second zone. The second zone is smaller than the first zone in a distance between a bottom surface and a ceiling surface. The coupling zone is configured such that the distance between the bottom surface and the ceiling surface thereof gradually decreases towards the second zone from the first zone. A connection zone provided in the main channel and connected to each of the pair of branch channels overlaps with the coupling zone.

7 Claims, 11 Drawing Sheets

MICROFLUIDIC DEVICE

The present application claims priority from Japanese Patent Application No. 2010-028265 filed on Feb. 10, 2010, the entire content of which is incorporated herein by reference.

BACKGROUND OF INVENTION

1. Field of the Invention

The present invention relates to a microfluidic device.

2. Description of the Related Art

In recent years, microfluidic devices have been used in analyzing liquid samples. The microfluidic device causes such a sample and another liquid to flow in each microchannel, and also causes chemical and biochemical reactions therein. Thus, a detection target material contained in the sample is detected (see, e.g., JP-A-2006-337221).

FIG. 10 illustrates a microfluidic device described in JP-A-2006-337221.

A microfluidic device 101 described in JP-A-2006-337221 electrochemically detects allergen contained in a sample. The microfluidic device 101 has a substrate 104 in which two substrate members 102 and 103 are stacked. A microchannel 105 is formed between the substrate members 102 and 103. The microchannel 105 includes a reaction portion 106, a detection portion 107, and a coupling portion 108 that connects the reaction portion 106 and the detection portion 107. An antibody specifically absorbing allergen contained in the sample is fixed in the reaction portion 106. An electrode 109 is provided with the detection portion 107.

A sample subjected to a pretreatment to link a predetermined enzyme to allergen is caused to flow in the microchannel 105. Allergen contained in the sample is trapped by the antibody fixed in the reaction portion 106. Then, a buffer solution containing a substrate-material to be changed by the enzyme linked to the allergen into an electrode active material is caused to flow in the microchannel 105. The substrate-material contained in the buffer solution is changed in a process, in which the buffer solution flows in the reaction portion 106, into an electrode active material by the enzyme linked to the allergen trapped in the reaction portion 106. The electrode active material reaches the detection portion 107 and acts upon the electrode 109 to thereby generate electric current. Allergen contained in the sample is detected by measuring the electric current.

In the device described in JP-A-2006-337221, the thickness (i.e., the distance between the bottom surface and the ceiling surface) of the microchannel at the detection portion 107 is set to be small, as compared with that at the reaction portion 106. This facilitates the action of the electrode active material upon the electrode 109. Accordingly, the sensitivity of the device may be enhanced.

SUMMARY OF INVENTION

In order to prevent the generation of air-bubbles and stabilize liquid-feeding, in the microfluidic device described in JP-A-2006-337221, the coupling portion 108 connecting the reaction portion 106 and the detection portion 107, which differ from each other in the thickness of the microchannel, is formed by being tapered so that the thickness of the microchannel gradually decreases towards the detection portion 107 from the reaction portion 106. However, air-bubbles may still be generated in the coupling portion 108.

FIG. 11 schematically illustrates liquid-feeding in the microfluidic device illustrated in FIG. 10.

Due to the surface tension of liquid L, a leading-part of the liquid L tends to go ahead of the rest thereof along each corner of the microchannel 105 and boundaries (hereinafter referred to generically as edges) of the substrate members 102 and 103, which are exposed to the microchannel 105. Although the edges similarly exist on both sides in the width direction of the microchannel 105, a leading-part of the liquid L flowing along the edge on one of the sides tends to go ahead of the rest of the liquid L (see FIG. 11A).

In the detection portion 107 at which the thickness of the microchannel is small as compared with that at the reaction portion 106, the flow rate of the liquid is high. Thus, the liquid rapidly expands to wet the surface thereof. Accordingly, a leading-part of the liquid goes ahead the rest thereof along the edge corresponding to one of sides in the direction of width of the coupling portion 108. When the liquid reaches the detection portion 107, an end part of the detection portion 107 is filled with the liquid before the subsequent part of the liquid reaches the detection portion 107. Thus, in the coupling portion 108, an air-bubble A is caught up to one of the sides in the direction of width of the coupling portion 108. Due to the air-bubble, the flow of the liquid becomes nonuniform in the direction of width of microchannel. Accordingly, stable liquid-feeding is disturbed (see FIGS. 11B to 11D).

The invention is accomplished in the above circumstances. An object of the invention is to provide a microfluidic device that achieves stable liquid-feeding.

According to the invention, there is provided a microfluidic device including a flowchannel in which liquid flows. The flowchannel includes a main channel and a pair of branch channels provided across the main channel from each other to be each connected to the main channel. The main channel includes a first zone, a second zone, and a coupling zone that connects the first zone and the second zone. The second zone is smaller than the first zone in distance between a bottom surface and a ceiling surface. The coupling zone is configured such that the distance between the bottom surface and the ceiling surface thereof gradually decreases towards the second zone from the first zone. A connection zone provided in the main channel and connected to each of the pair of branch channels overlaps with the coupling zone. The pair of branch channels are connected to the main channel at least in a zone in which the connection zone and the coupling zone overlap with each other, by striding across the bottom surface and the ceiling surface of the main channel, respectively.

According to the invention, an air-bubble is prevented from being caught up to one of the sides in the direction of width of the connection zone. Thus, stable liquid-feeding may be achieved.

DESCRIPTION OF EXEMPLARY EMBODIMENTS

Figure 1:
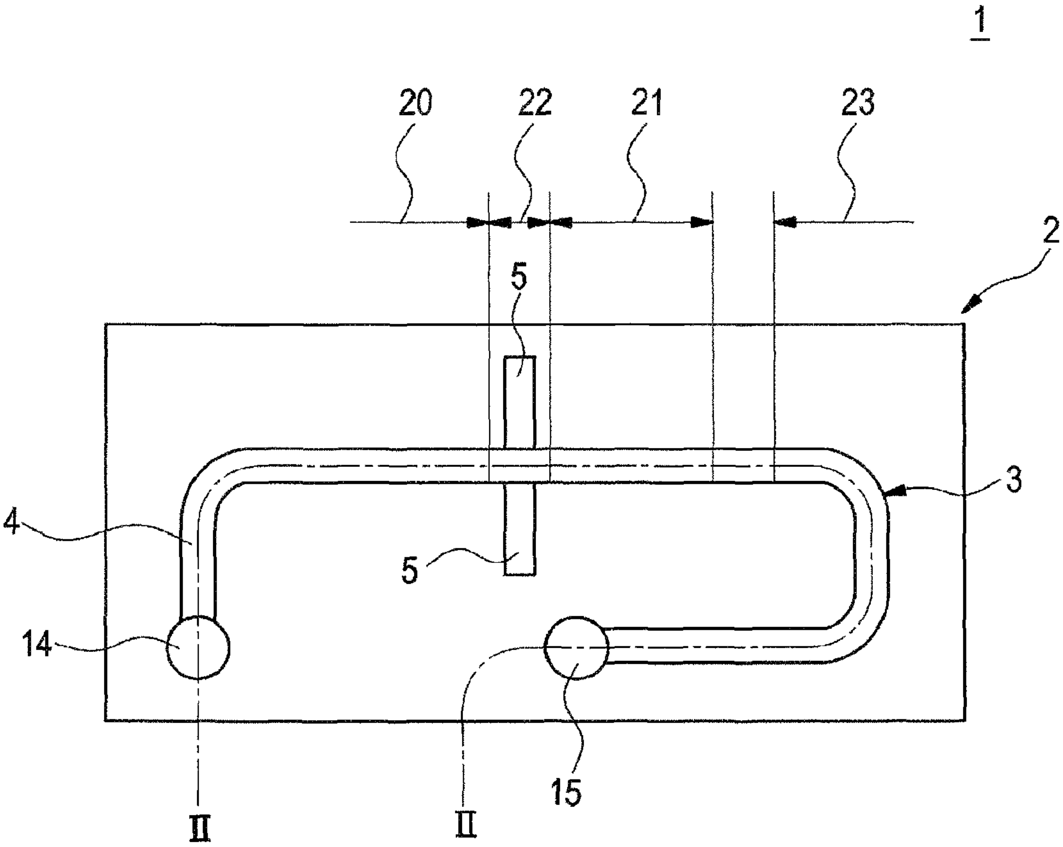
FIG. 1 is a diagram illustrating an example of a microfluidic device to describe an embodiment of the invention.
Figure 2:
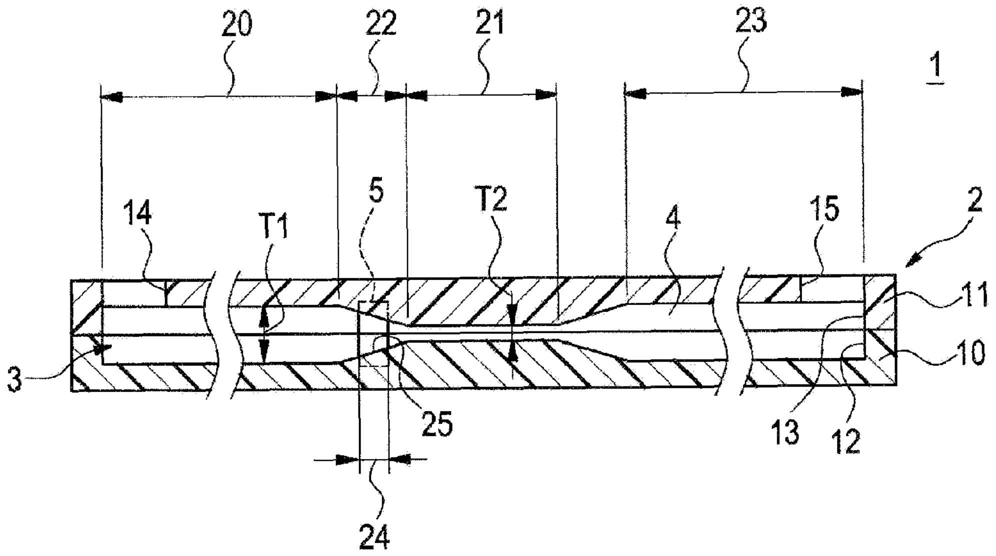
FIG. 2 is a diagram illustrating a cross-section of the microfluidic device, which is taken along line II-II illustrated in FIG. 1.

FIGS. 1 and 2 illustrate an example of a microfluidic device.

The microfluidic device to be described hereinafter causes liquid samples containing detection target materials to flow therein. Then, in a flowchannel, the microfluidic device traps the detection target material to which a marker substance adapted to emit light when excited is coupled. The detection target material is detected by observing the light emission of the marker substance coupled to the trapped detection target material. However, the microfluidic device according to the invention is not limited thereto. The invention may be applied to, e.g., a microfluidic device that electrochemically detects a detection target material, similarly to the above conventional device.

The microfluidic device 1 has a substrate 2. The substrate 2 is configured by stacking two substrate members 10 and 11. A microgroove 12 having a predetermined pattern is formed on the front surface of the substrate member 10 serving as a lower layer. A microgroove 13 having a predetermined pattern is formed in the back surface of the substrate member 11, which is contacted with the front surface of the substrate member 10. Two holes 14 and 15 are formed to penetrate through the back surface of the substrate member 11 in the direction of width thereof. The substrate member 11 is stacked on the substrate member 10. In addition, the microgroove 12 formed in the substrate member 10 is joined with the microgroove 13 formed in the substrate member 11. Thus, a flowchannel 3 is formed in the substrate 2. The hole 14 communicates with one end portion of the flowchannel 3 and serves as an introduction hole for introducing liquid such as a sample to the flowchannel 3. The hole 15 overlaps with the other end portion of the flowchannel 3 and serves as a discharge hole for discharging liquid having flowed through the flowchannel 3.

As described above, the microfluidic device 1 detects a detection target material by observing the light emission of the marker substance. Thus, at least one of the substrate members 10 and 11 is transparent. If the microfluidic device 1 electrochemically detects a detection target material, similarly to the above conventional technique, it doesn't matter whether the substrate members 10 and 11 are transparent.

For example, resin is used as the material of the substrate members 10 and 11. The grooves 12 and 13 for configuring the flowchannel 3 may be manufactured by injecting resin into a mold in which the patterns of the grooves 12 and 13 are formed, and then solidifying the resin. Alternatively, the grooves 12 and 13 may be manufactured by performing hot-embossing of the patterns of the grooves 12 and 13 on a resin flat-plate. In addition, the flowchannel may be configured by forming the groove only in one of the substrate members and covering the groove with the other substrate member.

The flowchannel 3 includes a main channel 4 and a pair of branch channels 5.

The main channel 4 includes an introduction zone (first zone) 20, a detection zone (second zone) 21, a coupling zone for connecting the introduction zone 20 and the detection zone 21, and a discharge zone 23. The introduction zone 20 is connected to an introduction hole 14. The discharge zone 23 is connected to a discharge hole 15.

A detection means for detecting a detection target material contained in a sample is provided in the detection zone 21. As described above, the microfluidic device 1 according to the present embodiment is configured to trap, in the flowchannel, a detection target material to which a marker substance adapted to emit light when excited is coupled, and to observe the light emission of the marker substance coupled to the trapped detection target material. Thus, the detection target material is detected. A means for trapping a detection target material is provided in the detection zone 21. For example, if the detection target material is an antigen such as allergen, an antibody for trapping the antigen by specifically absorbing the antigen is fixed onto the surface of the detection zone 21. The detection means is appropriately selected according to a method for detecting the detection target material. If the detection target material is electrochemically detected similarly to the above conventional technique, an electrode is provided on a surface of the detection zone 21.

The channel-thickness (distance between the bottom surface 30 and the ceiling surface 31) T2 at the detection zone 21 is small, as compared with the channel depth T1 at the introduction zone 20. The detection zone 21 is flat, as compared with the introduction zone 20. Consequently, the detection target material contained in the sample may easily be contacted with the surface of the detection zone 21 in which the detection means is provided. Thus, the detection sensitivity of the device may be improved. The channel-thickness T1 of the introduction zone 20 typically ranges 1 millimeters (mm) to 2 mm. Preferably, the channel-thickness T2 of the detection zone 21 is equal to or less than 0.2 mm so that the entire sample infiltrates due to a capillary force. The coupling zone 22 is tapered so that the channel-thickness at the coupling zone 22 gradually decreases towards the detection zone 21 from the introduction zone 20.

The pair of branch channels 5 are provided across the main channel 4 from each other to be each connected to the main channel 4. A connection zone 24 of the main channel 4, which is connected to the branch channels 5, i.e., a zone to which a connection port 25 of each branch channel 5 extends is included in the coupling zone 22. The entire connection zone 24 overlaps with the coupling zone 22. Thus, the connection port 25 of each branch channel 5 is opened only in the coupling zone 22. The connection zone 24 may be in agreement with the coupling zone 22. In addition, the connection zone 24 may extend to the introduction zone 20 or to the detection zone 21.

Figure 3:
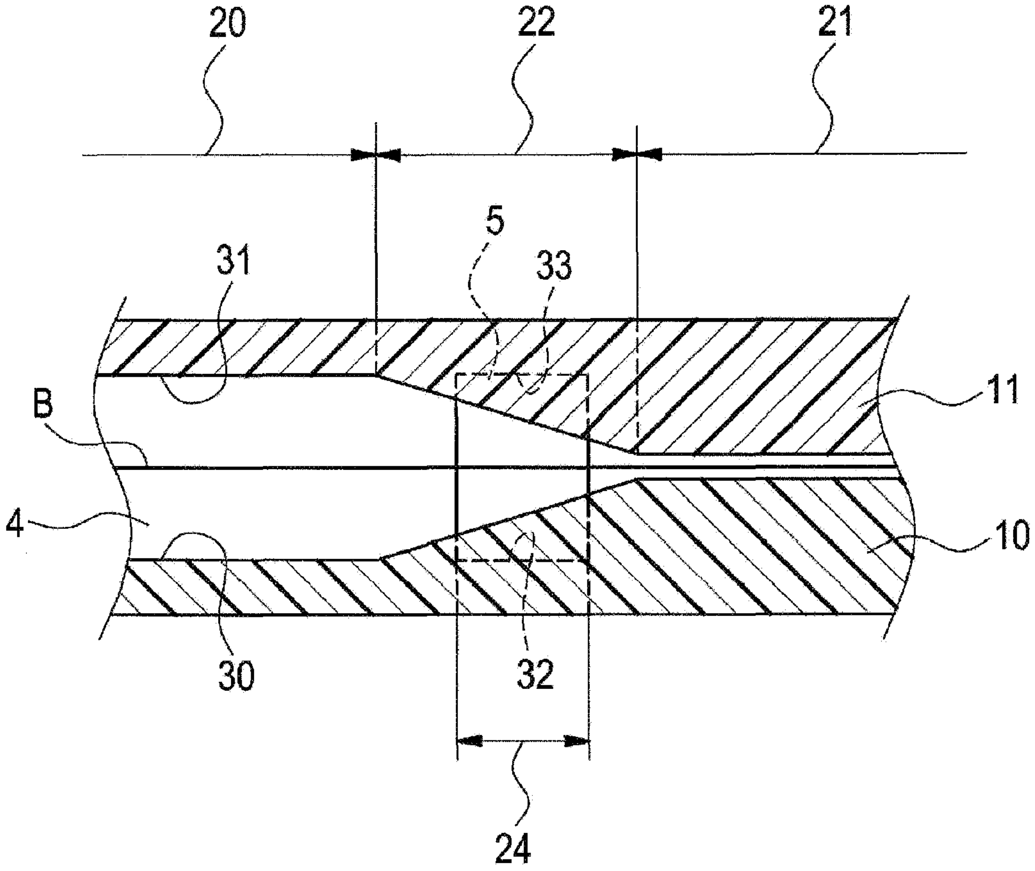
FIG. 3 is a diagram illustrating a connection place between a main channel and a pair of branch channels of the microfluidic device illustrated in FIG. 1.
Figure 4:
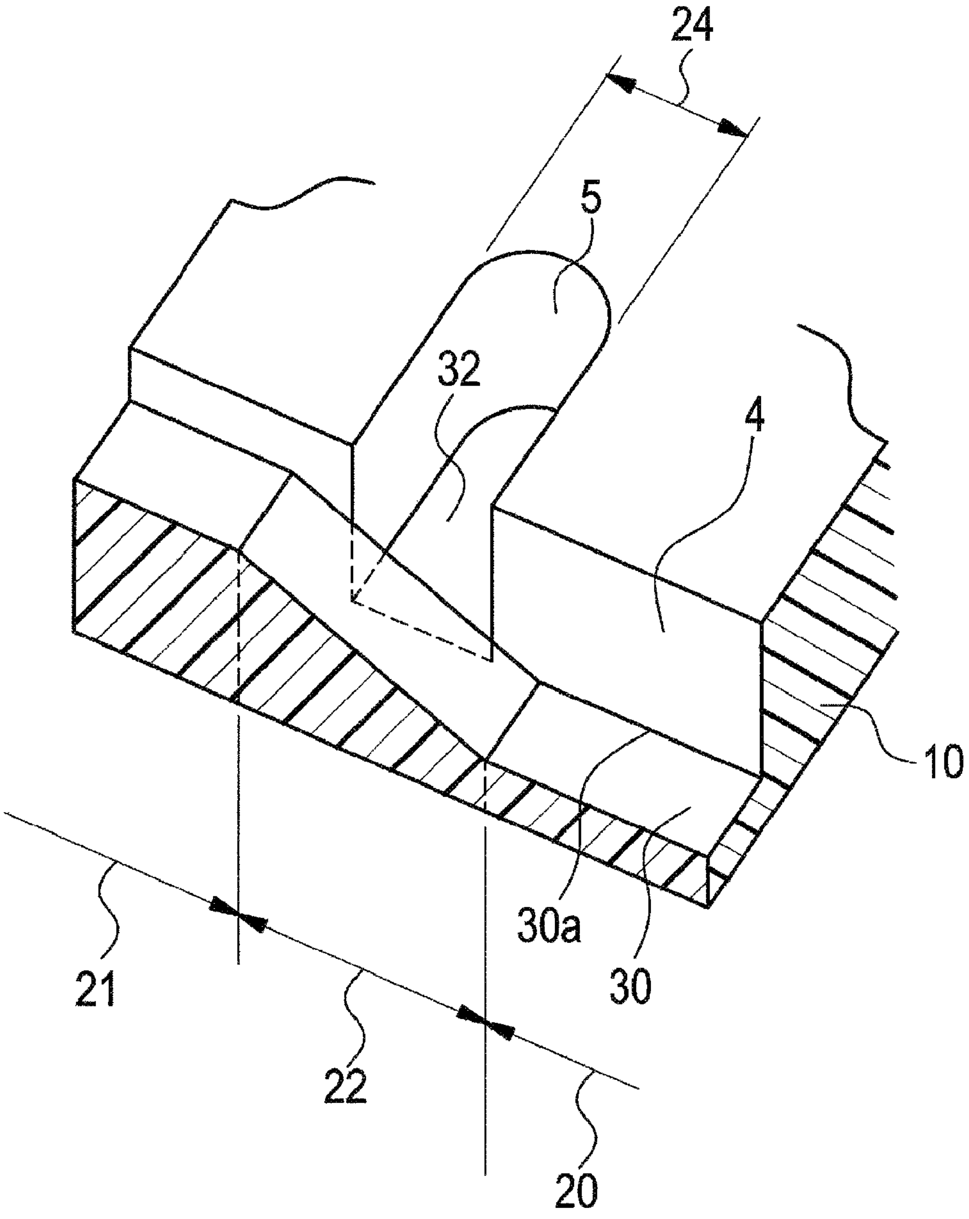
FIG. 4 is a diagram illustrating a connection place between the main channel and the pair of branch channels of the microfluidic device illustrated in FIG. 1.

FIGS. 3 and 4 illustrate the connection place between the main channel 4 and each of the pair of branch channels 5 illustrated in FIG. 1. However, FIG. 4 illustrates the connection place by omitting one of the substrate members.

The branch channels 5 are connected to the main channel 4 by striding across the bottom surface and the ceiling surface of the main channel 4, respectively. That is, the bottom surface 32 of the branch channel 5 is at a deeper position than the bottom surface 30 of the main channel 4, with respect to the front surface of the substrate 2. Thus, a step is formed between the bottom surface 32 of each branch channel 5 and the bottom surface 30 of the main channel 4. Accordingly, in the connection zone 24, a space is provided adjacent to each side edge 30*a* of the bottom surface 30 of the main channel 4. The ceiling surface 33 of each branch channel 5 is at a shallower position than the ceiling surface 31 of the main channel 4. Thus, a step is formed between the ceiling surface 33 of each branch channel 5 and the ceiling surface 31 of the main channel 4. Consequently, in the connection zone 24, a space is provided adjacent to a side edge of the ceiling surface 31 of the main channel 4.

The corners of the main channel 4 extend along the bottom surface 30 and the ceiling surface 31 thereof. Because the branch channels 5 are connected to the main channel 4 in the above manner, a space is provided adjacent to the side edge 30*a* of the bottom surface 30 and the side edge of the ceiling surface 31 of the main channel 4. Thus, the corners of the main channel 4 are separated at the connection zone 24.

Because the main channel 4 and the branch channels 5 are formed between the substrate members 10 and 11, the boundary B between the substrate members 10 and 11 is exposed between the bottom surface 30 and the ceiling surface 31 of the main channel 4 and between the bottom surface 32 and the ceiling surface 33 of the branch channels 5. In the connection zone 24, the branch channels 5 are connected to the main channel 4 by striding across the bottom surface 30 and the ceiling surface 31 thereof. Thus, the boundary B between the substrate members 10 and 11 always extends through the branch channels 5. In addition, because the branch channels 5 stride across the substrate members 10 and 11, the boundary B in plan view between the substrate members 10 and 11 is cut off in the branch channels 5.

Figure 5:
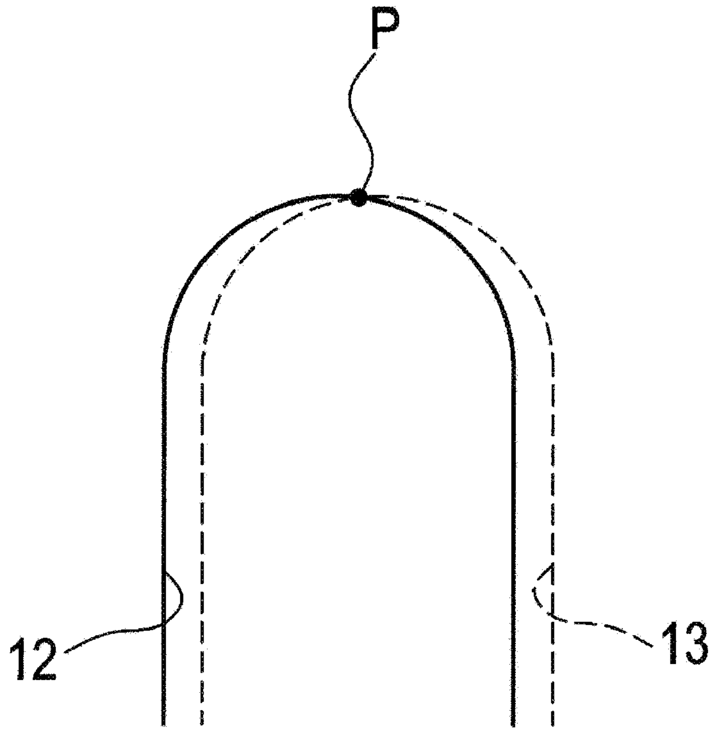
FIG. 5 is a plan diagram schematically illustrating the division of each edge in the branch channels of the micro fluidic device illustrated in FIG. 1.
Figure 6A:
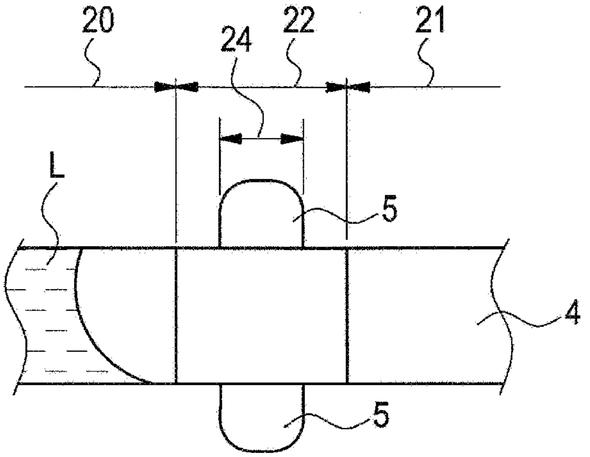
FIGS. 6A to 6D are diagrams schematically illustrating liquid-feeding performed in the microfluidic device illustrated in FIG. 1.
Figure 6B:
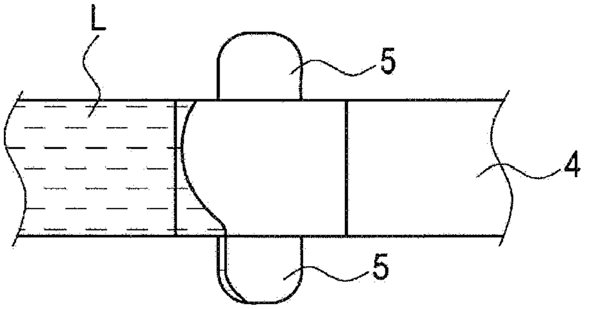
Figure 6C:
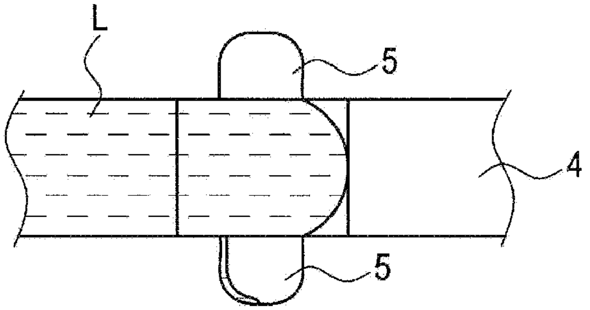
Figure 6D:
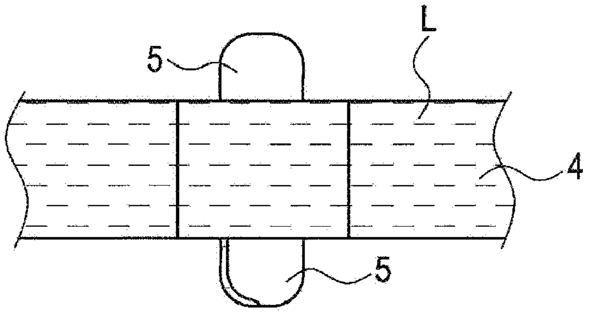

FIG. 5 schematically illustrates how the edges in plan view are divided in the branch channels 5.

In FIG. 5, a solid line represents an edge shown by projecting an edge of the groove 12 of the substrate member 10 configuring the branch channel 5 onto the front surface of the substrate member 10. A dashed line represents an edge shown by projecting an edge of the groove 13 of the substrate member 11 configuring the branch channel 5 onto the back surface of the substrate member 11.

The boundary B (see FIG. 3) between the substrate members 10 and 11 in the branch channels 5 includes the edge of the groove 12 of the substrate member 10 and that of the groove 13 of the substrate member 11, which are to be adjusted in position to each other. However, the edge of the groove 12 of the substrate member 10 intersects with that of the groove 13 of the substrate member 11 due to errors in the formation of the grooves 12 and 13 and the assembly of the substrate members 10 and 11. The boundary B between the substrate members 10 and 11 is disconnectedly divided at the point P of intersection between the edges.

A method for detecting an antigen such as allergen using the microfluidic device 1 configured as described above is briefly described hereinafter.

A pretreatment for coupling, to an antigen, a marker substance adapted to emit light when excited is performed on a liquid sample containing the antigen. Then, the sample subjected to the pretreatment is injected into the introduction hole 14. A decompression pump is connected to the discharge hole 15. Then, a pressure difference is caused between the introduction hole 14 and the discharge hole 15. Thus, the sample injected into the introduction hole 14 is drawn into the flowchannel 3. The sample is discharged from the discharge hole 15 through the introduction zone 20, the coupling zone 22, the detection zone 21, and the discharge zone 23. In a process in which the sample flows in the detection zone 21, the antigen contained in the sample is specially absorbed and trapped by the antibody fixed on the surface of the detection zone 21. Then, excitation light is irradiated onto the detection zone 21. The light emission of the marker substance coupled to the antigen trapped by the detection zone 21 is observed. The antigen contained in the sample is detected according to the presence and the intensity of light emission.

It has been described that the marker substance is made by the pretreatment to adhere to the antigen. However, the marker substance may be coupled to the antigen contained in the sample, in a process of causing the sample to flow in the introduction zone 20, by preliminarily making the marker substance to the surface of the introduction zone 20 or arranging, in the introduction zone 20, a carrier carrying the marker substance.

FIGS. 6A to 6D schematically illustrate liquid-feeding in the microfluidic device illustrated in FIG. 1.

As described above, a leading-part of liquid L flowing through the introduction zone 20 goes ahead of the rest thereof along one of the edges in the direction of width of the introduction zone 20 due to the surface tension of the liquid L. In the example illustrated in FIGS. 6A to 6D, a leading-part of the liquid L goes ahead of the rest thereof along the lower side, as viewed in the figure (see FIG. 6A).

The leading-part of the liquid L reaches the connection zone 22. Then, the leading-part of the liquid reaches an end at the side of the introduction zone 20 of the connection zone 24 connected to the branch channels 5. As described above, the corners of the main channel 4, which extend along the side edges of the bottom surface 30 and the ceiling surface 31 thereof are separated at the connection zone 24. In addition, as described above, the boundary B between the substrate members 10 and 11 extends through the branch channels 5. Thus, the leading-part of the liquid L going ahead along the edge flows into the branch channels 5 along the boundary B. However, in the main channel 4, the leading-part of the liquid L remains at the end at the side of the introduction zone 20 of the connection zone 24 or is restrained from going ahead of the rest thereof. To continually restrain, in a part up to the detection zone 21, the leading-part of the liquid L from going ahead along the edge, preferably, the connection zone 24 reaches the end at the side of the detection zone 21 of the coupling zone 22 or extends to the detection zone 21 over the end at the side of the detection zone 21 of the coupling zone 22 (see FIG. 6B).

While the leading-part of the liquid remains at the end at the side of the introduction zone 20 of the connection zone 24 in the main channel 4 or is restrained from going ahead of the rest thereof, the subsequent-part of the liquid catches up with the leading-part thereof. Then, the liquid flows through the coupling zone 22 such that a part of the liquid flowing through a substantially widthwise central portion of the coupling zone 22 goes ahead of the rest thereof. As described above, the boundary B between the substrate members 10 and 11 is disconnectedly divided in the branch channels 5. Thus, parts of the liquid respectively flowing into the branch channels 5 neither join together in the main channel 4 through the boundary B nor go ahead of the rest thereof (see FIG. 6C).

The leading-part of the liquid going ahead of the rest thereof through the substantially widthwise central portion of the coupling zone 21 gradually diffuses to both sides and then flow into the detection zone 21. Accordingly, an air-bubble is avoided from being caught up to one of the sides of the coupling zone 22. Thus, liquid-feeding is stabilized (see FIG. 6D).

Figure 7:
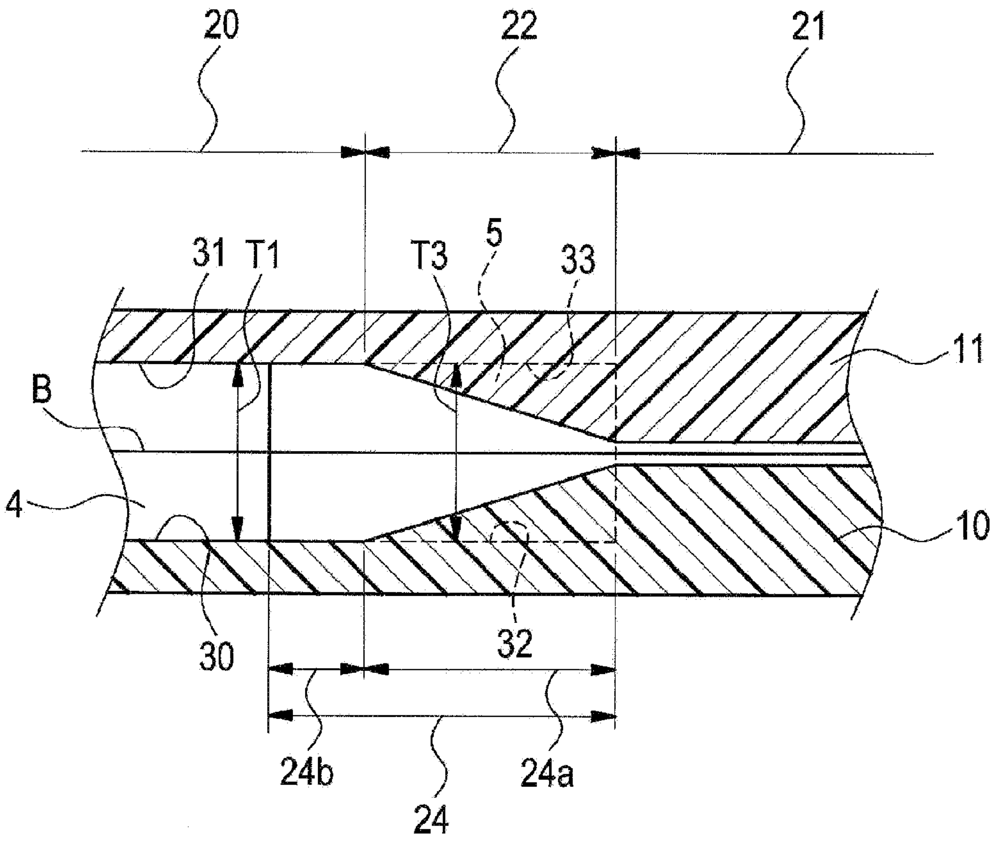
FIG. 7 is a diagram illustrating a connection place between the main channel and the pair of branch channels according to an example of a modification of the microfluidic device illustrated in FIG. 1.
Figure 8:
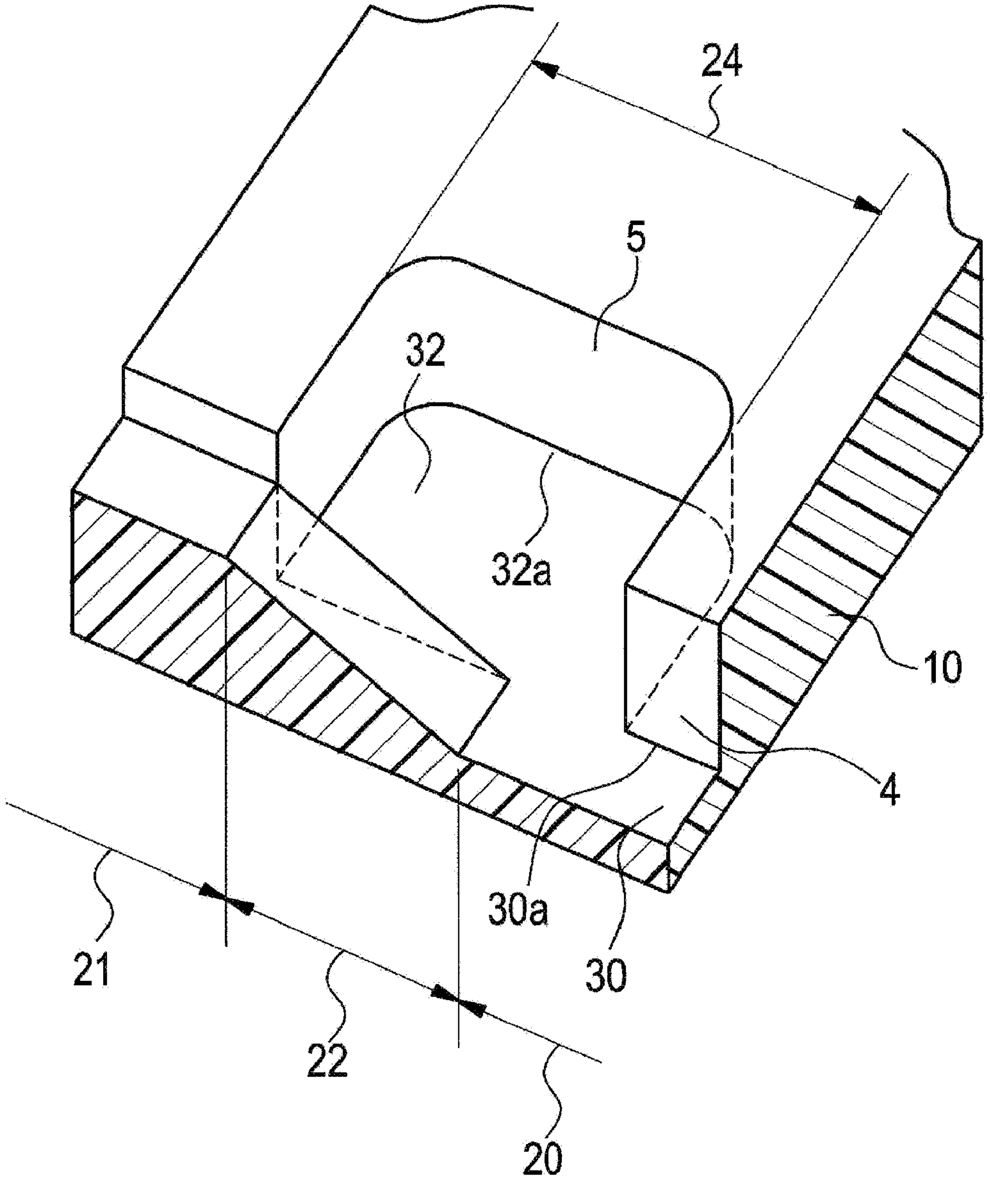
FIG. 8 is a diagram illustrating the connection place between the main channel and the pair of branch channels illustrated in FIG. 7.
Figure 9A:
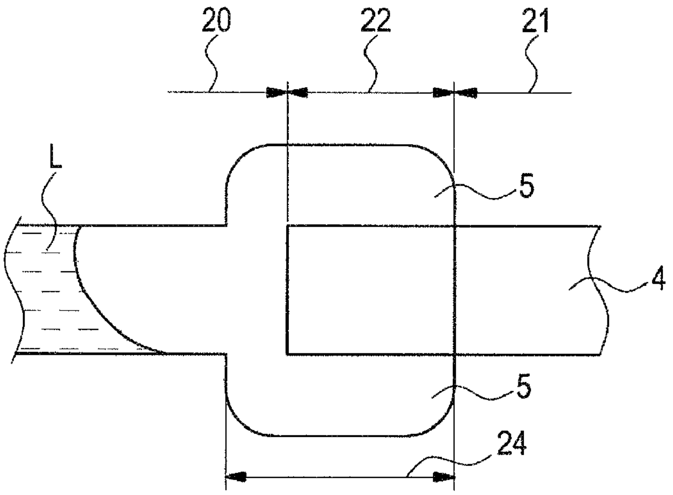
FIGS. 9A to 9D are diagrams schematically illustrating liquid-feeding performed in the microfluidic device illustrated in FIG. 7.
Figure 9B:
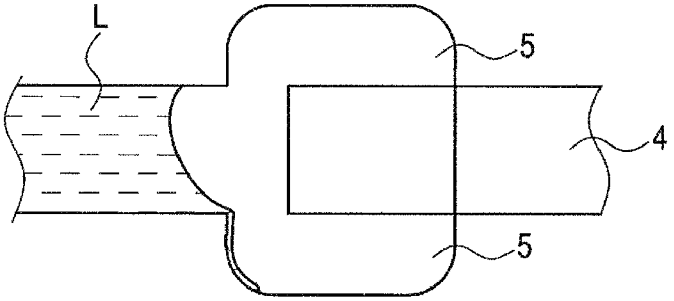
Figure 9C:
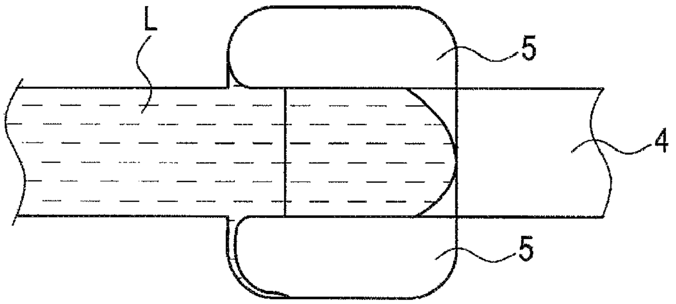
Figure 9D:
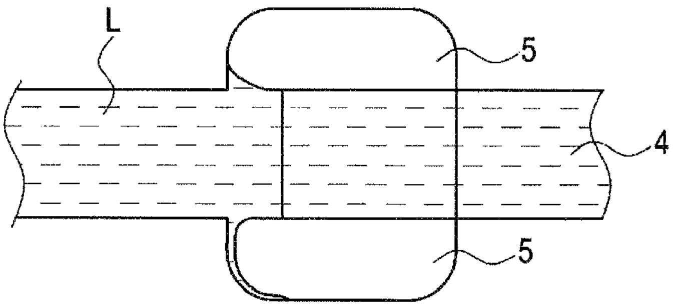
Figure 10:
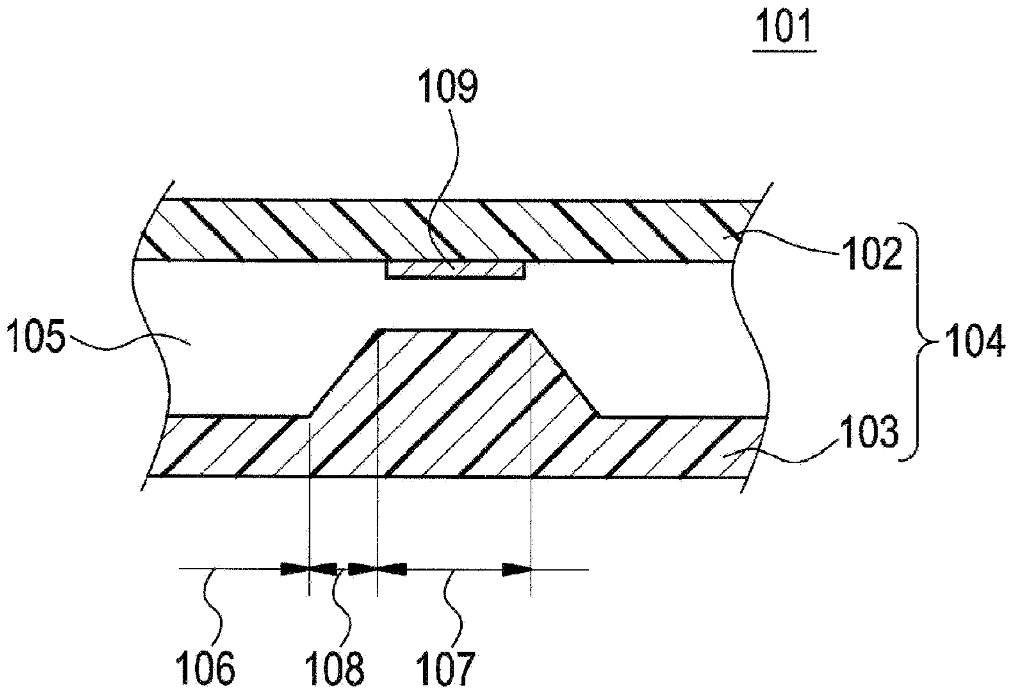
FIG. 10 is a diagram illustrating a conventional microfluidic device.
Figure 11A:
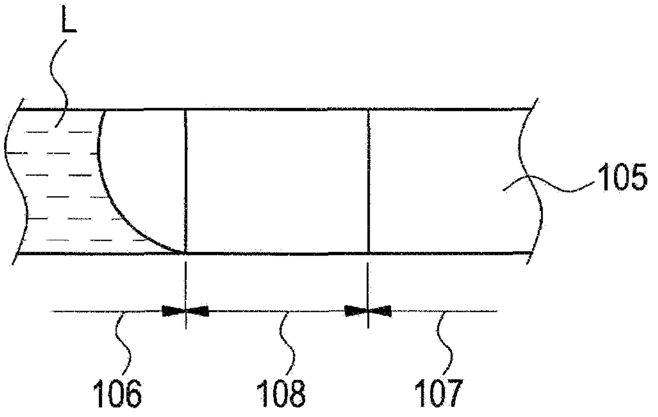
FIGS. 11A to 11D are diagrams schematically illustrating liquid-feeding performed in the microfluidic device illustrated in FIG. 10.
Figure 11B:
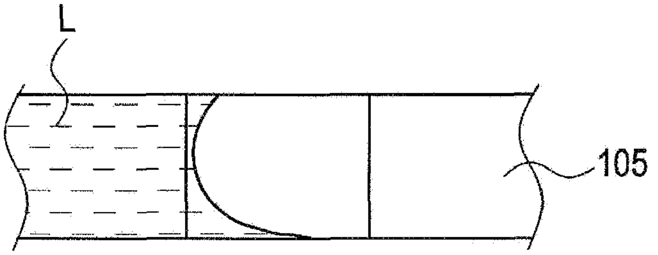
Figure 11C:
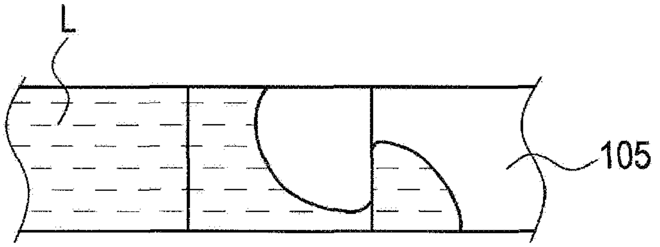
Figure 11D:
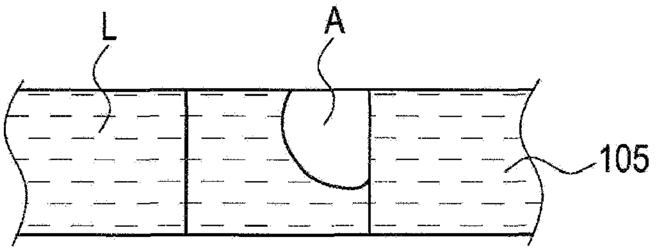

FIGS. 7 and 8 illustrate a connection place between the main channel and each of a pair of branch channels of an example of a modification of the microfluidic device illustrated in FIG. 1. FIG. 8 illustrates the connection place therebetween by omitting one of the substrate members.

In the microfluidic device illustrated in FIGS. 7 and 8, the connection zone 24 of the main channel 4, which is connected to the branch channels 5, extends from the end at the side of the detection zone 21 of the coupling zone 22 to the introduction zone 20. The channel-thickness T3 of each branch channel 5 is set to be equal to that T1 at the introduction zone 20 of the main channel 4. In a section 24*b* of the connection zone 24, which overlaps with the introduction zone 20, the bottom surface 32 of each branch channel 5 and that of the bottom surface 30 of the main channel 4 are positioned at the same depth with respect to the front surface of the substrate 2. Thus, the ceiling surface 33 of each branch channel 5 and that 31 of the main channel 4 are positioned at the same depth. That is, in the section 24*b*, the bottom surface 32 of each branch channel 5 is flush with the bottom 30 of the main channel 4. The ceiling surface 33 of each branch channel 5 is flush with that 31 of the main channel 4. In the section 24*a* of the connection zone 24, which overlaps with the coupling zone 22, the branch channels 5 are connected to the main channel 4 by striding across the bottom surface 30 and the ceiling surface 31.

The corners of the main channel 4 extend along the side edge 30*a* of the bottom surface 30 and the side edge of the ceiling surface 31 thereof, respectively. The corners of each branch channel 5 extend along the edge 32*a* of the bottom surface 32 and that of the ceiling surface 33, respectively. The branch channels 5 are connected to the main channel 4 in the above manner, so that the corners of the main channel 4 are connected to the corners of the branch channels 5 at the end on the side of the introduction zone 20 of the connection zone 24, i.e., at the near side of the coupling zone 22 to the introduction zone 20, respectively. The boundary B between the substrate members 10 and 11 is drawn into the branch channels 5 at the end at the side of the introduction zone 20 of the connection zone 24, i.e., at the near side of the coupling zone 22 to the introduction zone 20.

FIGS. 9A to 9D schematically illustrate the liquid-feeding in the micro fluidic device illustrated in FIG. 7.

As described above, a leading-part of the liquid flowing in the introduction zone 20 goes ahead along one of the widthwise side edges of the introduction zone 20 due to the surface tension thereof. In the example illustrated in the figure (i.e., FIG. 9A), the leading-part of the liquid goes ahead along the lower side, as viewed in FIG. 9A.

The leading-part of the liquid reaches the end at the side of the introduction zone 20 of the connection zone 24 connected to the branch channels 5. As described above, the corners of the main channel 4 are connected to those of the branch channels 5 there. The boundary B between the substrate members 10 and 11 is drawn into the branch channels 5 there. Thus, the leading part of the liquid flows into the branch channels 5 at the end of the side of the introduction zone 20 of the connection zone 24. In the main channel 4, the leading part of the liquid surely remains at the end at the side of the introduction zone 20 of the connection zone 24 (see FIG. 9B).

While the leading-part of the liquid remains at the end at the side of the introduction zone 20 of the connection zone 24, i.e., at the near side of the coupling zone 22 to the introduction zone 20, the subsequent-part of the liquid catches up with the leading-part thereof. Then, the liquid flowing in the main channel 4 flows through the connection zone 24 and the coupling zone 22 ranging therefrom (see FIG. 9C) so as to go ahead in the substantially widthwise central portion.

The leading-part of the liquid going ahead of the rest thereof through the substantially widthwise central portion of the coupling zone 22 gradually diffuses to both sides therefrom and then flow into the detection zone 21. Accordingly, an air-bubble is avoided from being caught up to one of the sides of the coupling zone 22. Thus, liquid-feeding is stabilized (see FIG. 9D).

Thus, the leading-part of the liquid is set to flow into the branch channels 5 at the end at the side of the introduction zone 20 of the connection zone 24, i.e., at the near side of the coupling zone 22 to the introduction zone 20. Accordingly, the leading-part of the liquid set in a state, in which the leading part thereof goes ahead in the substantially widthwise central portion of the main channel 4, may reach the coupling zone 22. Consequently, an air-bubble may more surely be avoided from being caught up to one of the sides of the coupling zone 22.

As described above, the microfluidic device disclosed in the present specification is a micro fluidic device including a flowchannel in which liquid flows. The flowchannel includes a main channel and a pair of branch channels provided across the main channel from each other to be each connected to the main channel. The main channel includes a first zone, a second zone, and a coupling zone that connects the first zone and the second zone. The second zone is smaller than the first zone in distance between a bottom surface and a ceiling surface. The coupling zone is configured such that the distance between the bottom surface and the ceiling surface thereof gradually decreases towards the second zone from the first zone. A connection zone provided in the main channel and connected to each of the pair of branch channels overlaps with the coupling zone. The pair of branch channels are connected to the main channel, at least in a zone in which the connection zone and the coupling zone overlap with each other, by striding across the bottom surface and the ceiling surface of the main channel, respectively.

The microfluidic device disclosed in the present specification is such that the connection zone reaches to the first zone, that a bottom surface of each of the pair of branch channels is flush with a bottom surface in the first zone of the main channel, and that a ceiling surface of each of the pair of branch channels is flush with a ceiling surface in the first zone of the main channel.

The microfluidic device disclosed in the present specification is such that the connection zone reaches an end at the side of the second zone of the coupling zone or reaches the second zone.

The microfluidic device disclosed in the present specification further comprises a substrate including a plurality of substrate members stacked therein. This microfluidic device is such that the main channel and the pair of branch channels are formed between the two substrate members adjacent to each other, and that the pair of branch channels strides across the two substrate members.

The microfluidic device disclosed in the present specification is such that liquid is infiltrated by a capillary force into the second zone.

The microfluidic device disclosed in the present specification is such that the distance between the bottom surface and the ceiling surface in the second zone is equal to or less than 0.2 mm.

The microfluidic device disclosed in the present specification is such that a detection means configured to detect a detection target material contained in liquid flowing in said second zone is provided in said second zone.

The microfluidic device disclosed in the present specification is such that the detection target material is an antigen, and that the detection means is an antibody specifically adsorbing the antigen.

What is claimed is:

1. A microfluidic device including a flowchannel in which liquid flows, wherein the flowchannel includes a main channel and a pair of branch channels provided across the main channel from each other to be each connected to the main channel, wherein the main channel includes a first zone, a second zone, and a coupling zone that connects the first zone and the second zone, wherein the second zone is smaller than the first zone in a distance between a bottom surface and a ceiling surface thereof, wherein the coupling zone is configured such that the distance between the bottom surface and the ceiling surface thereof gradually decreases towards the second zone from the first zone, wherein a connection zone provided in the main channel and connected to each of the pair of branch channels overlaps with the coupling zone, and wherein the pair of branch channels are connected to the main channel, at least in a zone in which the connection zone and the coupling zone overlap with each other, by striding across the bottom surface and the ceiling surface of the main channel, respectively wherein a detection unit configured to detect a detection target material contained in liquid flowing in the second zone is provided in the second zone.

2. The microfluidic device according to claim 1, wherein the connection zone reaches to the first zone, wherein a bottom surface of each of the pair of branch channels is flush with a bottom surface in the first zone of the main channel, and wherein a ceiling surface of each of the pair of branch channels is flush with a ceiling surface in the first zone of the main channel.

3. The microfluidic device according to claim 1, wherein the connection zone reaches an end at the side of the second zone of the coupling zone or reaches the second zone.

4. The microfluidic device according to claim 1, further comprises:

a substrate including a plurality of substrate members stacked therein, wherein the main channel and the pair of branch channels are formed between two of the substrate members adjacent to each other, and wherein the pair of branch channels strides across the two of the substrate members.

5. The microfluidic device according to claim 1, wherein liquid is infiltrated by a capillary force into the second zone.

6. The microfluidic device according to claim 1, wherein the distance between the bottom surface and the ceiling surface in the second zone is equal to or less than 0.2 mm.

7. The microfluidic device according to claim 1, wherein the detection target material is an antigen, and wherein the detection unit is an antibody specifically adsorbing the antigen.

* * * * *